United States Patent

Landers et al.

[11] Patent Number: 5,853,550
[45] Date of Patent: Dec. 29, 1998

[54] PROCESS FOR SEPARATING TAR FROM A REACTION MIXTURE

[75] Inventors: Robert Brent Landers, Ponca City, Okla.; Vijay Kumar Gupta, Hockessin, Del.; Vinci Martinez Felix, Kennett Square, Pa.

[73] Assignee: E. I. du Pont de Nemours and Company, Wilmington, Del.

[21] Appl. No.: 631,394

[22] Filed: Apr. 12, 1996

[51] Int. Cl.⁶ .................................................. B01D 3/36
[52] U.S. Cl. .................. 203/29; 203/67; 203/71; 203/94; 203/98; 570/177; 570/178
[58] Field of Search ................. 203/67, 98, 94, 203/29, 71; 570/177, 178

[56] References Cited

U.S. PATENT DOCUMENTS

| | | | |
|---|---|---|---|
| 952,833 | 8/1910 | Mantulo et al. | |
| 3,536,769 | 10/1970 | Seki et al. | 260/653.6 |
| 4,209,470 | 6/1980 | Lorquet | 260/652 |
| 4,766,258 | 8/1988 | Komatsu et al. | 570/168 |
| 4,911,792 | 3/1990 | Manzer et al. | 203/39 |
| 4,944,846 | 7/1990 | Manzer et al. | 203/1 |
| 4,968,850 | 11/1990 | Franklin et al. | 570/166 |
| 5,094,773 | 3/1992 | Manzer et al. | 252/172 |
| 5,105,033 | 4/1992 | Swearingen et al. | 570/177 |
| 5,367,102 | 11/1994 | Janssens et al. | 570/177 |
| 5,426,251 | 6/1995 | Komatsu et al. | 570/178 |

FOREIGN PATENT DOCUMENTS

| | | |
|---|---|---|
| 0 098 341 B1 | 1/1984 | European Pat. Off. . |
| 0098341 | 4/1986 | European Pat. Off. . |
| 0 187 643 A2 | 7/1986 | European Pat. Off. . |
| 637 579 A1 | 8/1995 | European Pat. Off. . |
| 62-246528 | 10/1987 | Japan . |
| 341788 | 6/1972 | U.S.S.R. . |

*Primary Examiner*—Jay H. Woo
*Assistant Examiner*—Betsey J. Morrison
*Attorney, Agent, or Firm*—James E. Shipley

[57] ABSTRACT

Disclosed is a process for the separation of tar and non-volatile reagents from a reaction mixture formed when chlorinated carbon compounds are allowed to react with anhydrous hydrogen fluoride in a liquid phase to form fluorinated carbon compounds. The disclosed process leaves tar essentially free of HF and in a form allowing for safe, easy, and economical transfer and disposal.

9 Claims, 2 Drawing Sheets

PROCESS FOR SEPARATING TAR FROM A REACTION MIXTURE

FIELD OF THE INVENTION

The present invention relates to a process for separating tar and non-volatile reagents from other reaction components in a liquid phase synthesis of fluorinated carbon compounds from halogenated carbon compounds and anhydrous hydrogen fluoride (HF).

BACKGROUND OF THE INVENTION AND PRIOR ART

The synthesis of fluorinated carbon compounds generally involves allowing halogenated carbon compounds to react with HF in a liquid phase, usually in the presence of a catalyst. In the practice of this process, undesirable non-volatile byproducts are formed. Techniques to separate these non-volatile byproducts from the reaction mixtures have been mentioned in the prior art. However, up to now, none of these techniques have proven successful.

Komatsu et al. (U.S. Pat. No. 4,766,258, issued Aug. 23, 1988) disclose a process for the manufacture of hydrofluorocarbons (HFCs) and hydrochlorofluorocarbons (HCFCs) in which the formation of high-boiling byproducts is presumably minimized. The process involves allowing hydrochlorocarbons to react with HF in the presence of a tin halide catalyst and an additive chosen from compounds containing oxygen or nitrogen. The "liquid withdrawing process" (column 7, line 41 of this reference) discloses separation of high-boiling byproducts from the remainder of the reaction components by using HF in an extraction step followed by distillation of the organic phase away from the high-boiling byproducts. The "vapor withdrawing process" (column 8, line 21 of this reference) discloses that such byproducts will accumulate in the reactor and are necessarily removed by withdrawing reaction aliquots in a continuous or batch-wise process followed by treatment. As to the specific nature of such treatment, Komatsu et al. are silent.

Komatsu et al. (Japanese Kokai publication number SHO 62[1987]-246528, publication date Oct. 10, 1987, describe a process for the manufacture of HFCs and HCFCs, characterized by allowing a "hydrogen-containing halogenated hydrocarbon" to react with HF in a liquid phase in the presence of the reaction product from a compound acting as a base in HF, a tin catalyst, and HF. This process is essentially the same as described in U.S. Pat. No. 4,766,258 with the exception that the additives of U.S. Pat. No. 4,766,258 are excluded here and the generic class of "compounds acting as bases in HF" are used in their place. This publication suffers the same deficiency as discussed previously for Komatsu et al.'s patent, U.S. Pat. No. 4,766,258.

Pennetreau et al. (EP 637,579 A1, published Feb. 8, 1995) disclose a method for the selective and high yield preparation of either HCFC-151a or HFC-152a by reaction of chloroethene with HF in the presence of a metal catalyst and an organic solvent composed of at least one saturated halogenated hydrocarbon. This process presumably provides a reduction in the amount of tar formed, but suffers several commercial deficiencies. A large percentage of solvent is required, thus reducing the effectiveness of the reactor by requiring a large volume reactor to accommodate the solvents; and, under such conditions, the failure of the process to form a substantial amount of the desirable HFC-152a over the undesirable HCFC-151a, is almost fatal to success. Furthermore, to prevent the concentration of tar from reaching a high level in the process, Pennetreau et al. require that the user regularly drain an amount of reaction mixture from the reactor. This reference is also silent regarding any technique for separating tar from the reaction components in the drained aliquot.

Pittard (EP 98,341 B) discloses a process in which HF is separated from the organic constituents of the reaction mixture resulting when 1,1,1-trichloroethane is allowed to react with anhydrous hydrogen fluoride in a liquid phase. In this process, vapor and liquid aliquots are withdrawn from a reactor; the liquid phase aliquot is heated to vaporize HF and other volatile organic materials; this vaporized material is combined with original reactor vapor phase aliquot; the resultant combination is cooled to about −26° C. to about −9° C.; and the HF-rich and halogenated hydrocarbon-rich phases are separated. After vaporizing the volatiles out of the liquid phase reactor aliquot, the remaining non-volatile tar, being about 2 mass % of the parent liquid phase, is removed to a water-containing disposal vessel.

OBJECTS OF THE INVENTION

It is an object of the invention to provide a process for the separation of tar and non-volatile reagents from other reaction components in the reaction mixture formed when halogenated carbon compounds are allowed to react with HF in a liquid phase, optionally in the presence of metal halide catalyst and other additives.

It is a further object to separate tar and non-volatiles when treating reaction mixtures obtained in the synthesis of 1,1-difluoroethane (HFC-152a), 1-chloro-1-fluoroethane (HCFC-151a) or mixtures thereof, where the starting halogenated carbon compound is at least one of chloroethene, fluoroethene, 1,1-dichloroethane, or 1-chloro- 1- fluoroethane (HCFC- 151a).

It is a still further object to so treat such reaction mixtures that are obtained in the synthesis of 1,1,-trifluoroethane (HFC-143a), 1-chloro-1,1-difluoroethane (HCFC-142b), 1,1-dichloro-1-fluoroethane (HCFC-141b) or mixtures thereof; where the appropriately starting halogenated carbon compound is 1,1-dichloroethene.

Other objects will appear hereinafter.

SUMMARY OF THE INVENTION

The objects are accomplished by a process wherein an aliquot is withdrawn from the reaction mixture; distilling from the aliquot a portion of the volatiles; combining with the non-volatiles remaining from distillation an effective amount of at least one saturated halogenated hydrocarbon solvent; and co-distilling the volatiles from the remaining portion of the reaction mixture plus saturated halogenated hydrocarbon solvent to provide a resultant composition essentially free of HF but consisting essentially of saturated halogenated hydrocarbon solvent, tar, and non-volatile reagents.

Thus, the present invention provides a process which maintains tar concentration in such a reaction mixture at a chosen level, separates tar from the other reaction components thereby allowing for recycle of the reaction components, and provides tar essentially free of HF that can be transferred and disposed of safely, easily, and economically.

DETAILED DESCRIPTION

Figure 1:
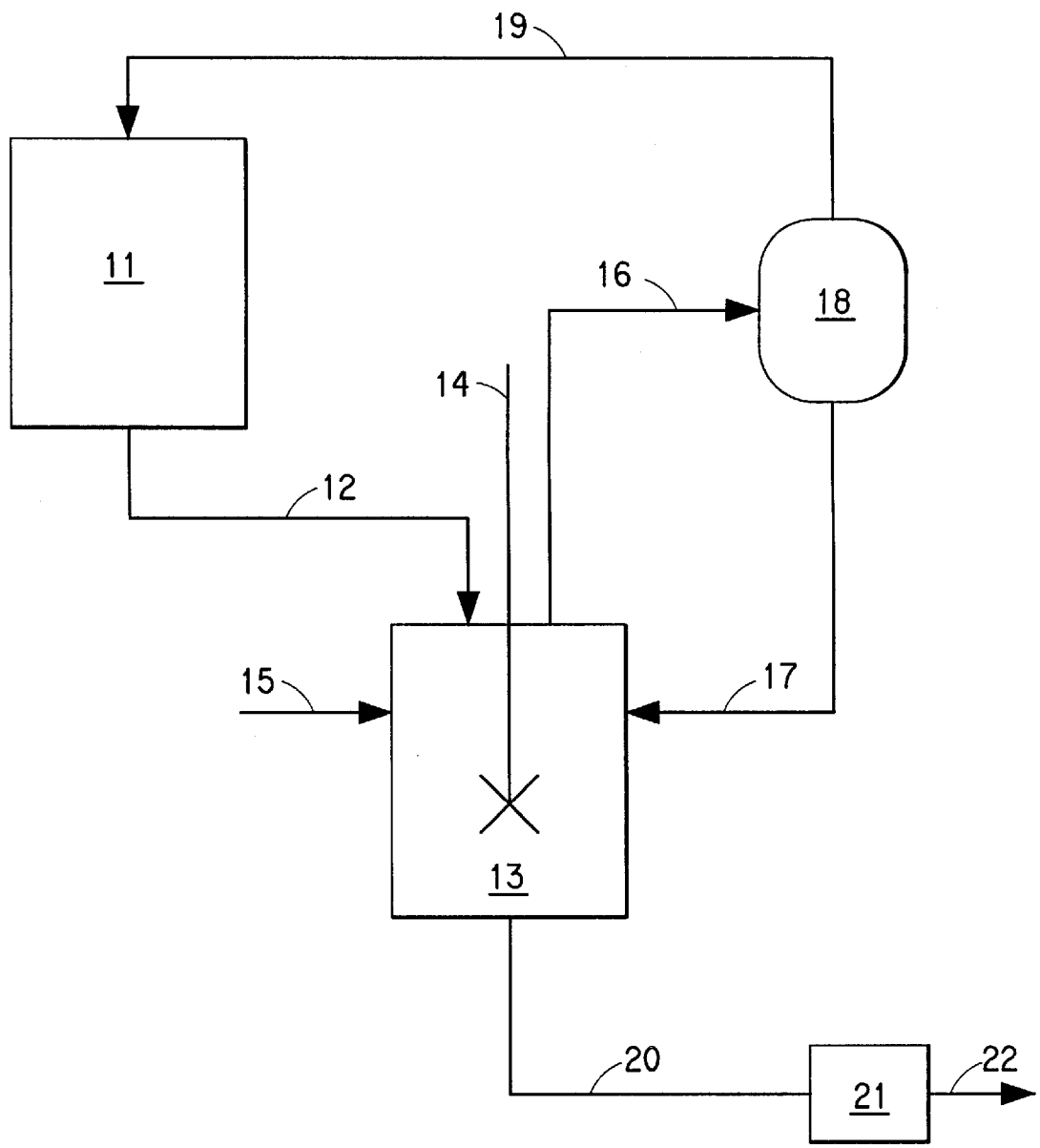
FIG. 1 is a schematic of one configuration of apparatus which may be employed to practice the present invention.

Fluorinated carbon compounds are of considerable utility as they may be used either alone or in blends with other materials as refrigerants, blowing agents for thermoplastic or thermoset foams, aerosol propellants, heat transfer media, cleaning agents, displacement drying agents, fire extinguishing agents, or as intermediates in the preparation of other compounds. HFCs, such as HFC-152a and HFC-143a, are environmentally acceptable replacements for chlorofluorocarbons (CFCs), since they have no known effect on the earth's stratospheric ozone.

Fluorinated carbon compounds may be produced by metal mediated exchange of the halogens (chlorine, bromine, and iodine) for fluorine in halogenated, usually chlorinated, carbon compounds. The process described herein is especially useful in treating halogen exchange reaction mixtures in which either HFC-152a or HFC-143a is being produced. HFC-152a may be produced through such a process from chlorinated carbon compounds such as 1,1-dichloroethane and HCFC-151a. A useful and preferred HFC-152a precursor is chloroethene, which will react with HF under exchange conditions to generate HFC-151a. HFC-143a may be produced through such a process from chlorinated carbon compounds such as 1,1-dichloroethene, HFC-141b, and HFC-142b.

The preparation of fluorinated carbon compounds by reacting halogenated carbon compounds with HF in a liquid phase, optionally in the presence of a metal halide catalyst and other additives, has been shown in the prior art to be complicated by the formation of undesirable non-volatile byproducts commonly referred to as "tar". Thus, tar-containing reaction mixtures may be obtained by any number of methods of the prior art, e.g., by reacting halogenated carbon compounds with HF in the presence of metal halide catalyst and other additives.

The term "tar" refers in one sense to compounds of fairly low molecular weight formed as a result of dimerization or trimerization of the halogenated carbon compounds and their fluorinated adducts. Tar further refers to higher molecular weight hydrocarbons, i.e., predominately molecular weights of about 50,000 the standard weight fraction distribution being from 2,000 to 75,000 number averaged molecular weight. These compounds may be branched, polymeric, halogenated hydrocarbons, which may contain metal species acquired from catalysts and any other additives that may be present. These higher molecular weight materials are formed by polymerization of lower molecular weight dimers, trimers, and oligomers with themselves or with the halogenated carbon compounds and their fluorinated adducts.

A usual tar-containing reaction mixture for treatment by the process of this invention is produced by reacting chloroethene with HF in the liquid phase in the presence of a tin(IV) halide catalyst and other additives. Such a process is described in recently filed co-pending U.S. patent applications: Ser. No. 08/474,884, filed Jun. 7, 1995now U.S. Pat. No. 5,714,650 ; Ser. No. 08/476,770, filed Jun. 7, 1995 (granted as U.S. Pat. No. 5,672,788 on Sep. 30, 1997); Ser. No. 08/778,439, filed Jan. 2, 1997; Ser. No. 08/778,427, filed Jan. 2, 1997; Ser. No. 08/583,331, filed Jan 5, 1996; and Ser. No. 08/597,745, filed Feb. 7, 1996 all of which are incorporated herein by reference. These processes generate tar-containing reaction mixtures of varied compositions, all of which are treatable by the process of the present invention.

The treatment of the present invention, by reducing "tar", enhances catalyst activity, promotes reaction selectivity, reduces reactor volume, and increases the yield of the desirable fluorinated carbon compound. When removed from the other reaction components, tar at room temperature is a light brown to black viscous and tacky material and is difficult to manipulate.

The terms "non-volatile reagent" and "metal halide catalyst" refer to at least one reagent or process derivative thereof in a reaction mixture which is non-volatile, i.e., does not exhibit an appreciable vapor pressure so as to undergo distillation when exposed to a temperature of at least 100° C. and a pressure of 1 atmosphere. Examples of such are the pure or mixed halides of Sn(IV), Sb(III), Sb(V), Ti(IV), Ta(V), Li(I), Na(I), and K(I), where the halides are at least one from the group consisting of fluoride, chloride, bromide, and iodide.

The term "other additives" refers to at least one reagent or process derivative thereof employed in a metal mediated halogen exchange reaction to improve product yield and selectivity, and to decrease byproduct formation. Additives with these attributes are described in the prior art section of this disclosure and are also the subject matter of the co-pending applications specified hereinbefore Examples of such additives are nitrogen-containing compounds such as ammonia ($NH_3$), organic amines; oxygen-containing compounds such as $H_2O$, $H_2O_2$, alcohols, ethers, aldehydes, ketones, carboxylic acids, esters, and epoxy compounds; phosphorous-containing compounds such as phosphines and phosphates; metal and non-metal alkoxides such as trialkyl borates, tetraalkyl silicates, and trialkyl phosphites, and alkali metal halides. Materials which are considered "other additives" may also be considered "non-volatile reagents" in instances where the definition applies.

In addition to use in the present process, it has been further established that minor amounts of saturated halogenated hydrocarbon solvents such as dichloromethane and HCFC-123, when employed in liquid phase exchange reactions employing Sn(IV) halide catalysis, lead to substantial benefits in reaction selectivity and yield. These processes are the subject of co-pending U.S. patent application Ser. No. 08/597,745, filed Feb. 7, 1996, which process can be employed in concert with the process of the present invention to provide further improvements. Thus, the use of the process of this invention avoids the rigorous separation of saturated halogenated hydrocarbon solvent from recycled HF as required in currently commercial processes.

A simplified statement of the present invention is, first-distilling components out of a reaction mixture to reach a desired composition, second-adding to this composition an amount of saturated halogenated hydrocarbon solvent, and third-distilling components out of the resultant composition to reach a final composition comprised of saturated halogenated hydrocarbon solvent, tar, and non-volatile reagents. Thus, the present invention can be described as a process for separating tar and non-volatile reagents from other reaction components in the synthesis of at least one fluorinated carbon compound in which at least one halogenated carbon compound is reacted in a liquid phase with HF, optionally in the presence of a metal halide catalyst and other additives, which involves (a) removal of an aliquot of reactor mass to another vessel;

(b) distilling a portion of components contained therein;

(c) adding a saturated halogenated hydrocarbon solvent to the non-distilled remainder; and, (d) distilling a portion of components contained therein to reach a composition comprised of saturated halogenated hydrocarbon solvent, tar, and non-volatile reagents.

Removal of the reactor mass in step (a) may be carried out in a batch-wise fashion. Continuous operation is also possible, but not necessary in most instances due to low rates of tar formation. The non-volatile nature of the tar requires that liquid aliquots of reaction mass be removed from the reactor at regular intervals to avoid reaching a tar concentration that inhibits reaction performance.

The reaction mass is a mixture of reaction components in liquid HF and may be transferred using techniques known in the art applicable to such corrosive liquids. In a preferred aspect of the invention involving synthesis of HFC-152a, the reactor mass of step (a) is a liquid mixture comprised of HCl, HFC-152a, chloroethene, HCFC-151a, HF, 1,1dichloroethane, Sn(IV) halides, alkali metal halides, tar, and various trace species indigenous to the process, e.g., fluoroethene. In another preferred aspect of the present invention involving synthesis of HFC-143a, the reactor mass of step (a) is a liquid mixture comprised of HCl, HFC-143a, HCFC-142b, HF, HCFC-141b, 1,1-dichloroethene, Sn(IV) halides, alkali metal halides, tar, and various trace species indigenous to the process.

The present process may generally be carried out on any scale desired, providing the basic components of an acid resistant vessel with heating capability, agitator, and sampling ports are present. The equipment and associated feed lines, effluent lines, and associated units should be constructed of materials resistant to HF and HCl. Typical materials of construction include stainless steels and high nickel alloys, such as Monel® nickel-copper alloys, Hastelloy® nickel-based alloys, and Inconel® nickel-chromium alloys.

Step (b) involves the use of standard distillation techniques to remove volatiles from the reaction mass taken in step (a). Such volatiles are typically removed to the point where the remainder contains from about 20 to about 70 mass % HF. Preferably, the remainder contains from about 25 to about 35 mass % HF and is of a viscosity that permits mechanical agitation and mixing with a saturated halogenated hydrocarbon solvent within a reasonable period of time at room temperature. The remainder after such distillation is comprised of HF, tar, and non-volatile reagents. Further distillation of HF to concentrate the remainder is not desirable. Such a procedure has been found to require rigorous conditions, i.e., higher temperatures and expensive equipment and, at best, results in a composition containing at least 20 mass % HF. This composition is unsafe as it contains an appreciable amount of HF and is a viscous and tacky material that is difficult to transfer.

Steps (c) and (d) involve addition of an amount of saturated halogenated hydrocarbon solvent to the remainder in step (b) followed by distillation. Through the addition of a saturated halogenated hydrocarbon solvent to the remainder from step (b) followed by distillation, the remaining HF is removed by co-distillation with said solvent under mild conditions. It is theorized that the saturated halogenated hydrocarbon solvates the HF, tar, and at least a portion of the non-volatile reagents and, in so doing, disrupts bonding interactions between HF and such components, thus allowing the remaining HF to co-distill out of the tar and non-volatile reagents with the solvent.

The saturated halogenated hydrocarbon solvents which may be used in the present invention are compounds which may be defined in a general sense by, but are by no intention limited to, the following properties:

First, such solvents are preferably miscible with the tar in the remainder from step (b) and preferably form a separate phase from the HF or form a low boiling azeotropic or azeotrope-like composition with the HF. Low boiling azeotrope and azeotrope-like compositions are preferred for use in the present process as they allow the HF and saturated halogenated hydrocarbon solvent to distill at a lower temperature than would be necessary to distill either of the pure components. Azeotropes useful in the present invention are known in the art, such as the azeotrope of HF/HFC-152a disclosed in co-pending U.S. patent application Ser. No. 08/474,884, filed Jun. 7, 1995 now U.S. Pat. No. 5,714,650, and the azeotrope of HF/HCFC-123 disclosed in U.S. Pat. No. 5,094,773 which issued Mar. 10. 1992.

Second, the saturated halogenated hydrocarbon solvents of the present invention must dissolve the tar and non-volatile reagents to concentrations preferably less than 70 mass % of the solvent, while remaining a tractable, low viscosity composition. Such properties allow for relatively easy transfer of the solvent, tar, and non-volatile reagent composition by simple techniques and minimize the amount of material requiring disposal.

Third, the saturated halogenated hydrocarbons used in the present invention should not cause an increase in phase miscibility between HF and other components such as HFC-152a or HCFC-123. This property allows for downstream separation of HF from process mixtures through a cooling and decantation process such as that described in U.S. Pat. No. 4,911,792 which issued Mar. 27, 1990.

The preferred saturated halogenated hydrocarbon solvents for use in the present invention are those which exhibit the previously described properties. Examples of such solvents include dichloromethane, trichloromethane, 1,1-dichloroethane, 2,2-dichloro-1,1,1-trifluoroethane (HCFC-123) and 1,2-dichloro-1,1,2-trifluoroethane (HCFC-123a). Most preferred of these saturated halogenated hydrocarbon solvents is HCFC-123.

Use of dichloromethane and/or trichloromethane as the solvent lead to the necessity for further downstream purification of the distillation streams. This is probably due to a small degree of reaction of dichloromethane with components of the exchange reaction mixture and the formation of chlorofluoromethane (HCFC-31) and difluoromethane (HFC-32). Such material are not desired in the distillation streams since they prove difficult to separate from fluorinated carbon compounds such as HFC-152a and HFC-143a. Use of trichloromethane usually yields small amounts of dichlorofluoromethane (HCFC-21) and chlorodifluoromethane (HCFC-22).

DESCRIPTION OF DRAWINGS

FIG. 1 is a schematic diagram of the process of the invention. A reactor 11 contains a liquid phase mixture formed by allowing a halogenated carbon compound to react with HF, optionally in the presence of metal halide catalyst and other additives. A liquid phase purge from reactor 11 is transferred through line 12 to stripper 13. In the preparation of HFC-152a, by allowing chloroethene to react with HF in a liquid phase in the presence of tin(IV) halides, this purge typically contains HF (72.5 mass %), HCl (0.5%), HFC-152a (8%), tar (10%), and tin(IV) halides (9%). Agitator 14 is activated; the total stripper pressure is set between 10 psig and 140 psig; and the contents of stripper 13 are heated.

Volatiles (HCl, HF, and HFC-152a in the case of the HFC-152a process) are removed from the stripper 13 through line 16 for further processing in vessel 18, until the remainder contains from about 20 to 70 mass % HF. For the specific HFC-152a process previously mentioned, the remainder after this step of the process is comprised of HF (47 mass %), tar (28%), and tin(IV) halides (25%). The saturated halogenated hydrocarbon solvent, optionally also containing some HF recycled from the recovery system, and fresh saturated halogenated hydrocarbon is added through line 15 to stripper 13. The amount of HF added with the recycle solvent is hopefully and at most 20% of the mass of the remainder, preferably less than 10%, and the amount of fresh saturated halogenated hydrocarbon added is typically between 100% and 1000% of the mass of the remainder, preferably about 500% in the case of HCFC-123 and somewhere within the range of 100–1000% depending upon the specific saturated halogenated hydrocarbon solvent used.

Stripper 13 contents are then heated to a temperature between 20° C. and 100° C. at pressures between 10 psig and 140 psig, and the volatiles, primarily HF and saturated halogenated hydrocarbon solvent, (with trace amounts of HFC-152a in the HFC-152a process) are removed through line 16 for further processing in vessel 18. After removal of such volatiles in the HFC-152a process, the remainder typically contains tar (18 mass %), tin(IV) halides (16%), and saturated halogenated hydrocarbon solvent (66%). This material is heated to a temperature between 40° C. and 110° C. under pressures of between 10 psig and 140 psig, and excess saturated halogenated hydrocarbon solvent is vaporized and removed from stripper 13 through line 16 for further processing in vessel 18. Saturated halogenated hydrocarbon solvent is so removed until the mass ratio of [saturated halogenated hydrocarbon]:[tar+non-volatile reagents] remaining in stripper 13 is between 0.5:1 and 5:1, preferably about 2:1. The saturated halogenated hydrocarbon, tar, and non-volatile reagents remaining in stripper 13 are then transferred through line 20 to storage vessel is 21. If desired, this remainder may be transferred through line 22 for appropriate disposal. Stripper 13 is then ready to accept another reactor purge for treatment by the process of this invention.

Means of further processing the volatiles distilled out of stripper 13 are disclosed in the art and, generally, depend upon the specific saturated halogenated hydrocarbon solvent employed in the process. The saturated halogenated hydrocarbon solvent may be separated from HF, HFC-152a, and other reaction components by employing processes such as those disclosed by Manzer et al. U.S. Pat. No. 5,094,773 which issued Mar. 10, 1992 and relates to separating HCFC-123/HF azeotropes; and Manzer et al. U.S. Pat. No. 4,944,846 which issued Jul. 31 1990 and relates to separating HCFC-123/HF mixture; and Manzer et al. U.S. Pat. No. 4,911,792 which issued Mar. 27, 1990 relating to HFC-123/HF mixture and Mahler et al. in U.S. patent application Ser. No. 08/474,884, filed Jun. 7, 1995, now U.S. Pat. No. 5,714,650 relating to separating azeotropic or azeotrope-like compositions of HF with dihaloethanes. Saturated halogenated hydrocarbon solvent purified by any of the foregoing processes may be recycled through line 17 to stripper 13 for repeated use in the invented process. HF purified by any similar process may be optionally further refined by processes known in the art and recycled through line 19 to reactor 11.

EXAMPLES

The following examples are offered to further illustrate the present invention.

Example 1
Employing HCFC-123 as Saturated Halogenated Hydrocarbon Solvent

A sample of reactor mass was taken from an HFC-152a synthetic run in which chloroethene was reacted with HF in the presence of $SnCl_4$. The 163 g sample contained in a 150 cc stainless steel cylinder at 19° C. and approximately 30 psig was vented of volatiles to atmospheric pressure. The remaining 129 g of reactor mass was transferred to a Teflon® bottle containing a Teflon® coated magnetic stirbar. Approximately 366 g of HCFC-123 was added, the bottle placed in a 24° C. to 28° C. bath, and stirring begun. The volatile species were allowed to further vent.

After addition of the HCFC-123 charge, the contents of the bottle consisted of two phases; HCFC-123 on the bottom and HFC-152a reactor mass on the top. The bottle was weighed at intervals of 10 minutes and visually observed for changes. After 40 minutes, the mass of the bottle had decreased from over 450 g to 230 g, and a single phase was present. The sample at this point was black and had a low viscosity (<100 cp by visual observation versus a standard). The sample was allowed to continue venting, and viscosity was first seen to substantially increase when 54 g of material remained in the bottle. The sample was further vented until only 27 g of viscous, tacky material remained. At this point, 100 g of HCFC-123 was added to the bottle and the sample immediately became less viscous. The sample was then allowed to further vent. The sample again become viscous and tacky when the mass reached approximately 27 g.

The final composition of the sample as measured by ion selective electrodes (chloride and fluoride ions), X-ray fluorescence spectrometry (tin), and mass difference (tar and HCFC-123) was: 2.5 g fluoride, 0.04 g chloride, 0.9 g of tin, 15.6 g of tar, and 8 g HCFC-123.

Comparative Example 1
Employing No Solvent

A sample of reactor mass was taken from an HFC-152a synthetic run in which chloroethene was reacted with HF in the presence of $SnCl_4$ and NaCl. The sample was comprised of 7 mass % organic tar, 12 mass % tin(IV) salts, and 2 mass % sodium salts, with the balance being HF, HCl, and HFC-152a. The 319 g sample contained in a 300 cc stainless steel cylinder was slowly vented from 30 psig to atmospheric pressure at 21° C. removing 44 g of volatiles. The remaining 275 g of reactor mass was transferred to a Teflon® bottle containing a Teflon® coated magnetic stirbar.

The bottle was placed in a 26° C. to 29° C. bath, stirring begun, and volatiles were swept out of the sample. The bottle was massed at intervals of 10 minutes and visually observed for changes. The initial sample, after venting to atmospheric pressure, was a black, non-viscous, single phase with a mass ratio of HF to non-volatile reagents of 3.1. After 60 minutes, 172.5 g of reactor mass remained with a mass ratio of HF to non-volatile reagents of 1.6. By visual observation, the physical properties of the sample had not changed at this time. After 90 minutes, visual observation revealed changes in the sample's physical properties. The sample had been reduced to 134 g, the mass ratio of HF to non-volatile reagents was 1.0, and the viscosity of the sample had increase to a state similar to an average latex paint at room temperature. A small amount of solids could be seen coming out of solution after 140 minutes of heating. The sample mass was now 99 g, the mass ratio of HF to nonvolatile reagents was 0.5, and the viscosity by visual observation was the same paint-like consistency with some solids present. After approximately 5 hours venting at between 26° C. to 29° C., the sample was a black solid conformed to the shape of the bottle.

The sample mass was now 88.3 grams and the mass ratio of HF to non-volatile reagents was 0.3.

Example 2
Employing Dichloromethane as Saturated Halogenated Solvent

A sample of reactor mass was taken from an HFC-152a synthetic run in which chloroethene was reacted with HF in the presence of $SnCl_4$. The 163 g sample contained in a 150 cc stainless steel cylinder at 21° C. and approximately 30 psig was vented of volatiles to atmospheric pressure. The remaining 127 grams of reactor mass was transferred to a Teflon® bottle containing a Teflon® coated magnetic stir-bar. Approximately 254 g of dichloromethane was then added, the bottle placed in a 30° C. to 43° C. bath, and stirring begun. The volatile species were allowed to further vent. The bottle was weighed at intervals of 10 minutes and visually observed for changes.

By visual observation, the reactor mass sample together with dichloromethane was observed to contain two liquid phases; dichloromethane on the bottom and HFC-152a reactor mass on the top. Both phases were non-viscous and no solids were visible. As the sample volatiles were allowed to vent, the first substantial change in viscosity could be seen when 127 g of sample remained in the bottle. The sample continued to thicken and formed a very viscous, solid containing mixture when 46 g of material remained. At this point, an additional 100 g of dichloromethane was added and the solids were dissolved. The sample was then allowed to continue venting, and the sample again became viscous and tacky when the mass reached 46 grams. The sample was then heated until solids formed with 22 grams of sample remaining.

The final composition of the sample as measured by ionic specific electrode (fluoride ions), X-ray fluorescence spectrometry (tin), and mass difference (tar and dichloromethane) was: 4 g fluoride, 2 g tin, 13 g tar, and 3 g dichloromethane.

Example 3
Employing Trichloromethane as Saturated Halogenated Solvent

A sample of reactor mass was taken from an HFC-152 synthetic run in which chloroethene was reacted with HF in the presence of $SnCl_4$. The 151 g sample contained in a 150 cc stainless steel cylinder at 21° C. and 30 psig was vented of volatiles to atmospheric pressure. The remaining 129 g of reactor mass was transferred to a Teflon® bottle containing a Teflon® coated magnetic stir-bar. Approximately 389 grams of trichloromethane was added, the bottle placed in a 24° C. to 31° C. bath, and stirring begun. The volatiles were allowed to further vent. The bottle was weighed at intervals of 10 minutes and visually observed for changes.

By visual observation, the reactor mass sample together with trichloromethane was observed to contain two liquid phases; trichloromethane on the bottom and HFC-152a reactor mass on the top. Both phases were non-viscous and no solids were visible. After 70 minutes, the sample in the bottle had decreased to 374 g from 499 g and only a single, non-viscous phase was present. The sample was further vented until 321 g sample remained showing essentially no change in physical properties by visual observation.

The final composition of the sample as measured by ion specific electrode (fluoride ion), X-ray fluorescence spectroscopy (tin), and mass difference (tar and trichloromethane) was: 2 g fluoride, 21 1 g tin, 26 g tar, and 292 g trichloromethane.

Figure 2:
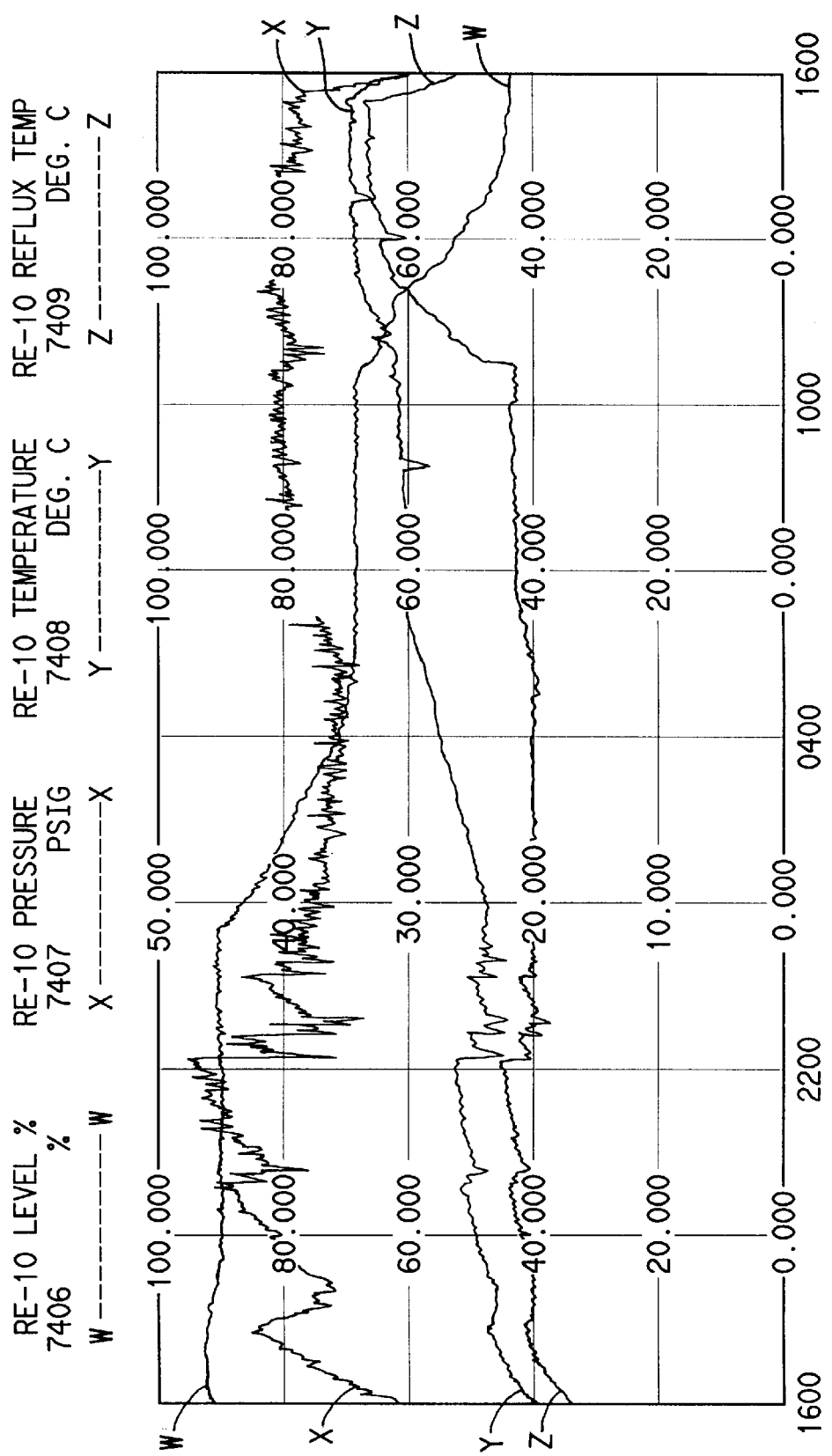
FIG. 2 is a plot of time (hour) versus reactor level (%), reactor total pressure (psig), liquid phase temperature (°C.), and vapor phase temperature (°C.) for one embodiment of the present invention as described in Example 4.

Example 4 (and accompanying FIG. 2 )
Employing HCFC-123 as Saturated Halogenated Solvent A 2 L, Hastelloy® C-276, agitated reactor was charged with 1395 g of HCFC-123 and 279 g of HFC-152a process reactor mass. The HFC-152a reactor mass originated from a HFC-152a synthetic run in which chloroethene was allowed to react in a liquid phase with HF in the presence of $SnCl_4$. The total pressure in the reactor was maintained at 40 psig using a back pressure regulator, and heat input was maintained at 0.375 Kw using an electric heating mantle around the reactor body. The liquid and vapor temperature, level, and pressure were monitored as volatile components were distilled. FIG. 2 shows the change in these variables over time. The vapor temperature most accurately reflects the composition of the volatile material being removed from the reactor. The constant vapor temperature as reactor level falls from 90% to 70% reflects the removal of the HF/HCFC-123 azeotrope. The vapor temperature (reflux temp on FIG. 2) of 40° C. corresponds with the predicted temperature for the HF/HCFC-123 azeotrope at 40 psig. The increase in vapor temperature as the reactor level goes from 70% to 45% reflects an increase in composition of HCFC-123 in the vapor. At the end of the run, the vapor temperature starts to level at 70° C.; the boiling point for pure HCFC-123 at 40 psig. Following the distillation and prior to removal of the excess HCFC-123, 534 g of sample remained.

The final composition of the sample as measured by ion specific electrodes (fluoride ion), X-ray fluorescence spectrometry (tin), and mass difference (tar and HCFC-123) was: 8 g fluoride, 5 g tin, 30 grams of tar, and 491 g HCFC-123.

What is claimed is:

1. A process for separating tar and non-volatile reagents from hydrogen fluoride and other reaction components of a reaction mixture formed in the production of 1,1-difluoroethane (HFC-152a) wherein hydrogen fluoride and at least one halogenated carbon compound selected from the group consisting of chloroethene, fluoroethene, 1,1-dichloroethane, and 1-chloro-1-fluoroethane (HCFC-151a) are allowed to react in a liquid phase, optionally in the presence of metal halide catalyst and other additives, comprising the steps of:
   (a) removing a liquid phase aliquot from the reaction mixture,
   (b) distilling a first portion of components from the liquid phase aliquot to form a remainder,
   (c) combining with the remainder at least one saturated halogenated hydrocarbon solvent and optionally HF, and
   (d) distilling a second portion of components comprising HF and saturated halogenated hydrocarbon solvent therefrom resulting in a composition comprising saturated halogenated hydrocarbon solvent, tar, and non-volatile reagents.

2. The process of claim 1 wherein said reaction mixture further comprises from 0 to 5 mass % of at least one compound selected from the group consisting of dichloromethane and 2,2-dichloro-1,1,1-trifluoroethane (HCFC-123).

3. The process of claim 1 wherein said saturated halogenated hydrocarbon solvent is at least one compound selected from the group consisting of dichloromethane, trichloromethane, 1,1-dichloroethane, 1-chloro-1-fluoroethane (HCFC-151a), 1,1-difluoroethane (HFC-152a), 2,2-dichloro-1,1,1-trifluoroethane (HCFC-123), 1,2-dichloro-1,1,2-trifluoroethane (HCFC-123a).

4. The process of claim 1 wherein distilling said first portion in step (b) results in a remainder comprising from about 20 to about 70 mass % HF.

5. The process of claim 1 wherein the amount of saturated halogenated hydrocarbon added in step (c) is between 1 to 10 times the mass of said remainder.

6. The process of claim 1 wherein distillate in steps (b) and (d) comprises at least one of HF, HCl, 1,1-difluoroethane (HFC-152a), 1-chloro-1-fluoroethane (HCFC-151a), 1,1-dichloroethane, dichloromethane, trichloromethane, 2,2-dichloro-1,1,1-trifluoroethane (HCFC-123), and 1,2-dichloro-1,2-trifluoroethane (HCFC-123a).

7. The process of claim 1 wherein distillate removed in steps (b) and/or (d) is an azeotropic composition.

8. The process of claim 7 wherein said azeotropic composition is at least one of HF/2,2-dichloro-1,1,1-trifluoroethane (HCFC-123), HF/1,2-dichloro-1,1,2-trifluoroethane (HCFC-123a), and HF/1,1-difluoroethane (HFC-152a).

9. The process of claim 1 wherein said resulting composition of step (d) comprises from about 0.5:1 to about 5:1 mass ratio of saturated halogenated hydrocarbon solvent-to-tar plus non-volatile reagents.

* * * * *